US012653966B2

(12) United States Patent
Gavin

(10) Patent No.:  US 12,653,966 B2
(45) Date of Patent:  Jun. 16, 2026

(54) MULTI-STAGE INJECTION DEVICE

(71) Applicant: West Pharmaceutical Services, Inc.,
Exton, PA (US)

(72) Inventor: William David Gavin, Phoenix, AZ
(US)

(73) Assignee: West Pharmaceutical Services, Inc.,
Exton, PA (US)

( * ) Notice: Subject to any disclaimer, the term of this
patent is extended or adjusted under 35
U.S.C. 154(b) by 760 days.

(21) Appl. No.: 18/023,407

(22) PCT Filed: Aug. 27, 2021

(86) PCT No.: PCT/US2021/047868
§ 371 (c)(1),
(2) Date: Feb. 27, 2023

(87) PCT Pub. No.: WO2022/051176
PCT Pub. Date: Mar. 10, 2022

(65) Prior Publication Data
US 2023/0347074 A1      Nov. 2, 2023

Related U.S. Application Data

(60) Provisional application No. 63/072,967, filed on Sep.
1, 2020.

(51) Int. Cl.
*A61M 5/46* (2006.01)
*A61M 5/31* (2006.01)
*A61M 5/32* (2006.01)

(52) U.S. Cl.
CPC ............ *A61M 5/46* (2013.01); *A61M 5/3135*
(2013.01); *A61M 5/3243* (2013.01)

(58) Field of Classification Search
CPC .... A61M 5/46; A61M 5/3135; A61M 5/3243;
A61M 5/178; A61M 5/28; A61M 5/3202;
(Continued)

(56) References Cited

U.S. PATENT DOCUMENTS

| | | | | |
|---|---|---|---|---|
| 9,233,213 B2* | 1/2016 | Olson | ................. | A61M 5/3129 |
| 2013/0289480 A1* | 10/2013 | Roberts | ............... | A61M 5/3204 |
| | | | | 604/110 |
| 2015/0165129 A1* | 6/2015 | Row | ................. | A61M 5/31501 |
| | | | | 604/189 |

FOREIGN PATENT DOCUMENTS

| | | | |
|---|---|---|---|
| EP | 2468338 A1 | 6/2012 |
| WO | 2004047892 A1 | 6/2004 |

(Continued)

*Primary Examiner* — Kevin C Sirmons
*Assistant Examiner* — Leah J Swanson
(74) *Attorney, Agent, or Firm* — Blank Rome LLP

(57) ABSTRACT

An injection device (10) includes a lower housing (18), a
sleeve (32) supported by the lower housing, and a syringe
spring (34) received within the sleeve. The spring supports
a syringe (12). A needle guard (26) is proximally slidable
relative to the lower housing from a first position, concealing
the syringe needle (12b), to a second position. A needle
guard spring (27) biases the needle guard distally relative to
the lower housing. An upper housing (16) is distally slidable
relative to the lower housing from a pre-use position to a
dispensed position. Movement of the needle guard from the
first position to the second position extends the distal tip of
the needle distally beyond the needle guard by a first
distance. Subsequent distal movement of the upper housing
relative to the lower housing from the pre-use position
toward the dispensed position advances the distal tip of the
needle distally further beyond the needle guard by a second
distance.

13 Claims, 4 Drawing Sheets

(58) Field of Classification Search
CPC .... A61M 5/2033; A61M 5/24; A61M 5/2425;
A61M 5/281; A61M 5/3137; A61M
5/31571; A61M 5/31578; A61M 5/3158;
A61M 5/31591; A61M 5/3245; A61M
5/3257; A61M 5/326; A61M 5/3269;
A61M 5/3271; A61M 5/3272; A61M
5/3273; A61M 5/3275; A61M 2005/2013;
A61M 2005/208; A61M 2005/2403;
A61M 2005/2407; A61M 2005/2411;
A61M 2005/3199; A61M 2005/3247;
A61M 2005/3258; A61M 2005/3261;
A61M 2005/3263; A61M 2005/3264;
A61M 2005/3265; A61M 2005/3267;
A61M 2005/3268
See application file for complete search history.

(56)                References Cited

FOREIGN PATENT DOCUMENTS

| WO | 2012093075 | A1 | 7/2012 |
|----|------------|----|--------|
| WO | 2021030066 | A1 | 2/2021 |

* cited by examiner

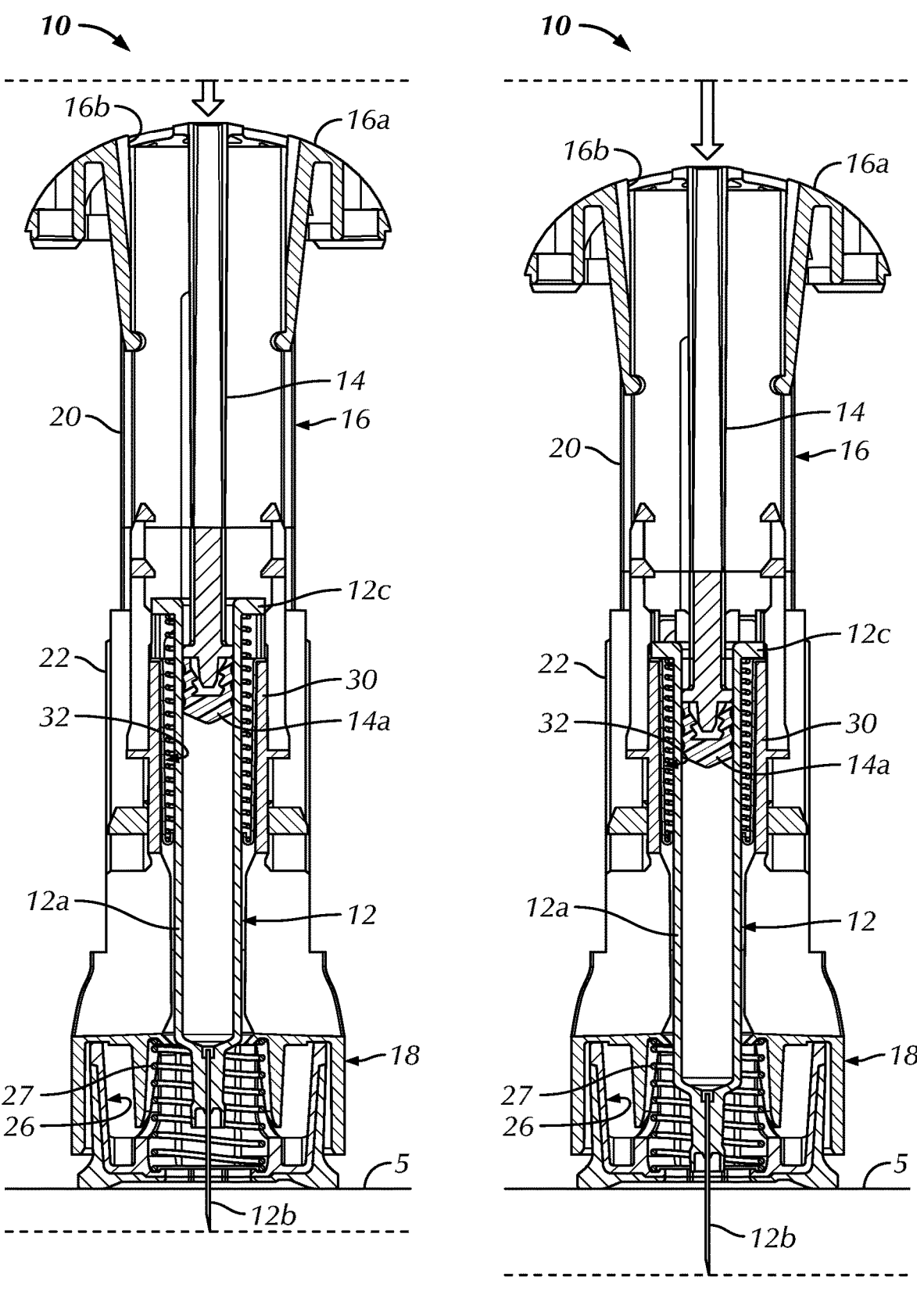
*FIG. 3*                    *FIG. 4*

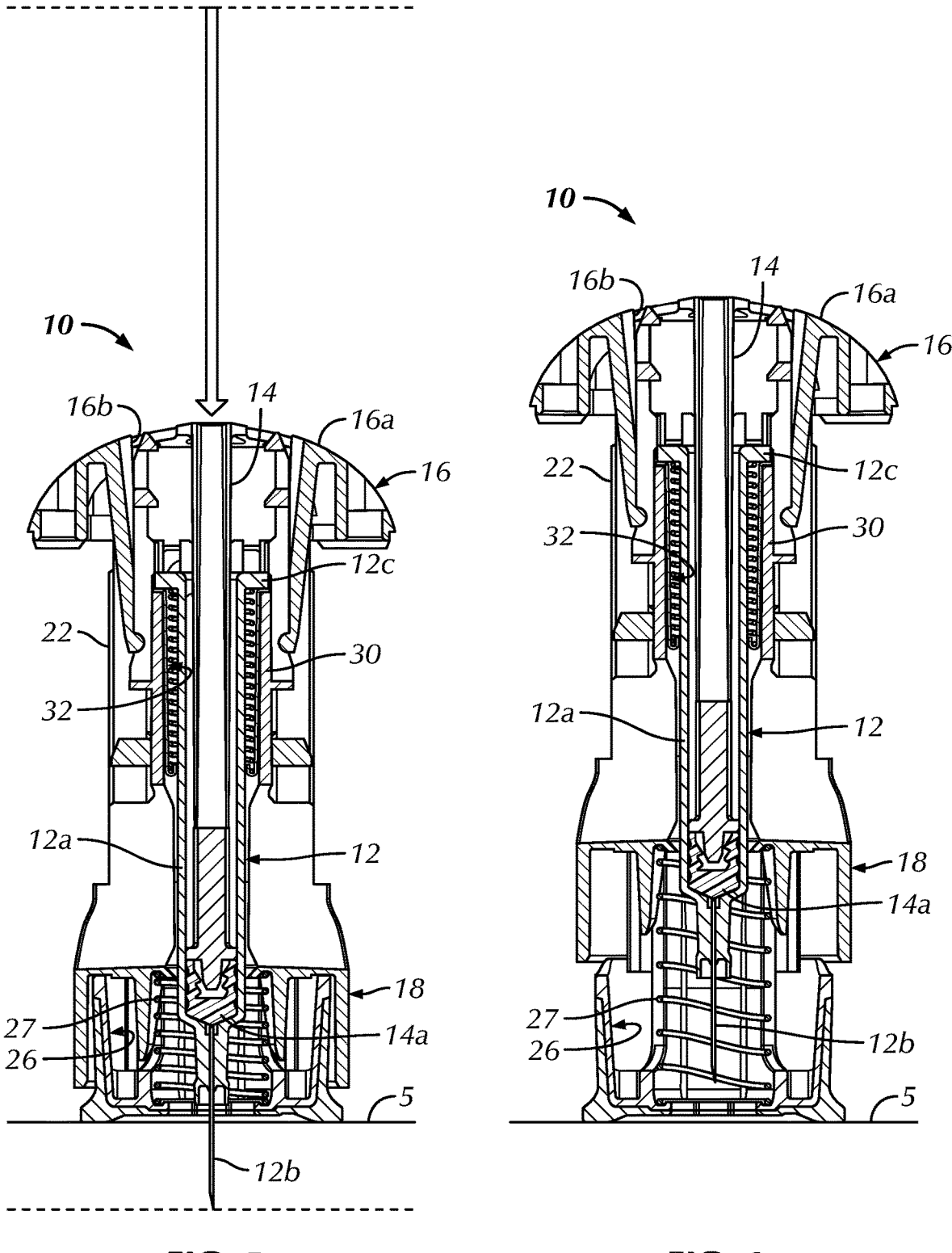
FIG. 5           FIG. 6

MULTI-STAGE INJECTION DEVICE

CROSS-REFERENCE TO RELATED APPLICATION

This application is a National Stage of International Patent Application No. PCT/US2021/047868, filed Aug. 27, 2021, which claims priority from U.S. Provisional Patent Application No. 63/072,967, filed Sep. 1, 2020, the entire contents of which are hereby incorporated by reference herein.

BACKGROUND OF THE DISCLOSURE

The disclosure generally relates to injection devices for administering parenteral medicament injections, and, more particularly, to injection devices containing pre-filled syringes.

Conventional injection devices for administering parenteral medicament injections are designed to either accommodate a particularly sized syringe and/or needle or to administer the medicament at a generally single depth underneath the skin surface of a user/patient. One drawback of such injection devices is that different injection device components must be manufactured for each intended syringe and/or needle size for use therewith and intended needle depth.

It would, therefore, be advantageous to manufacture an injection device capable of accommodating differently sized syringes and/or needles and capable of administering injections at different pre-determined objective depths underneath the skin surface while maximizing the number of common injection device components.

BRIEF SUMMARY OF THE DISCLOSURE

Briefly stated, one aspect of the present disclosure is directed to an injection device configured to administer a medicament from a syringe having a syringe barrel at least partially filled with the medicament and sealed by a piston, a flange extending radially from a proximal end of the syringe barrel, and a needle extending distally from a distal end of the syringe barrel. The device includes a lower housing, a spring retaining sleeve supported by the lower housing, and a syringe spring at least partially received within the spring retaining sleeve, wherein the spring is configured to support an underside of the flange of the syringe when installed so as to support the syringe within the lower housing such that the needle protrudes from a distal end of the lower housing. A needle guard is in sliding engagement with the lower housing, and is movable relative to the lower housing in a proximal direction from a first position, wherein a distal end of the needle guard extends beyond the distal end of the lower housing, is spaced from a proximal end of the lower housing by a first interval, and is configured to conceal a distal tip of the needle when the syringe is installed in the lower housing to a second position, wherein the distal end of the needle guard is spaced from the proximal end of the lower housing by a second interval that is less than the first interval. A needle guard spring is configured to engage the lower housing and the needle guard to bias the needle guard distally relative to the lower housing. An upper housing is in sliding engagement with the lower housing and movable relative to the lower housing in a distal direction from a pre-use position to a dispensed position. The upper housing may optionally be prevented from distal movement relative to the lower housing when the needle guard is in the first position. Proximal movement of the needle guard from the first position to the second position is configured to extend the distal tip of the needle distally beyond the needle guard by a first distance when installed. Optionally, proximal movement of the needle guard from the first position to the second position may also be configured to permit distal movement of upper housing relative to the lower housing. Subsequent distal movement of the upper housing relative to the lower housing from the pre-use position toward the dispensed position is configured to (i) first compress the syringe spring, and, in turn, distally translate the needle relative to the lower housing when installed, such that the distal tip of the needle extends distally beyond the needle guard by a second distance that is greater than the first distance, and (ii) thereafter, further advance the upper housing distally relative to the syringe when installed to dispense the medicament from the syringe.

In one configuration, the spring retaining sleeve defines a passage extending therethrough from a proximal end to a distal end, the syringe spring being positioned at least partially within the passage. A flange extends radially from the proximal end and is configured to engage the lower housing to support the spring retaining sleeve. A support is disposed within the passage to support a distal end of the syringe spring.

In any of the previous configurations, the syringe spring is configured to define a stiffness resulting in a spring compression force that is less than a force of static friction between the piston and the syringe barrel when the syringe is installed within the lower housing.

In any of the previous configurations, the distal movement of the upper housing relative to the lower housing is configured to translate therewith a plunger rod engaging the piston, wherein distal translation of the plunger rod first causes the compression of the syringe spring, and subsequently advances the piston through the syringe barrel to dispense the medicament from the syringe In any of the previous configurations, the upper housing is positionally locked relative to the lower housing when the upper housing reaches the dispensed position. In one configuration, the needle guard spring is configured to bias the needle guard from the second position to a third position when the upper housing is locked in the dispensed position. In the third position: the distal end of the needle guard extends beyond the distal end of the lower housing, the distal end of the needle guard is spaced from the proximal end of the lower housing by a third interval greater than the first interval, and the distal end of the needle guard is configured to conceal the distal tip of the needle of the syringe when installed. In one configuration, the needle guard is positionally locked relative to the upper and lower housing in the third position thereof.

In any of the previous configurations, the first distance is less than 10 mm.

In any of the previous configurations, the second distance is at least 10 mm greater than the first distance. In one configuration, the second distance is between approximately 10 mm and approximately 80 mm.

In any of the previous configurations, the injection device further includes the syringe installed within the lower housing.

BRIEF DESCRIPTION OF THE SEVERAL VIEWS OF THE DRAWINGS

The following description of the disclosure will be better understood when read in conjunction with the appended drawings. It should be understood, however, that the disclosure is not limited to the precise arrangements and instrumentalities shown. In the drawings:

FIG. 3 is a cross-sectional elevational view of the injection device of FIG. 1 placed on a skin surface, with an injection needle penetrating the skin surface to a first depth prior to inj ection;

FIG. 4 is a cross-sectional elevational view of the injection device of FIG. 1 placed on a skin surface, with the injection needle penetrating the skin surface to a second depth prior to inj ection;

FIG. 5 is a cross-sectional elevational view of the injection device of FIG. 1 placed on a skin surface, with the injection needle penetrating the skin surface to the second depth after injection is complete;

FIG. 6 is a cross-sectional elevational view of the injection device of FIG. 1 after injection is complete, with the needle retracted within the injection device.

DESCRIPTION OF THE DISCLOSURE

Figures 1, 2:
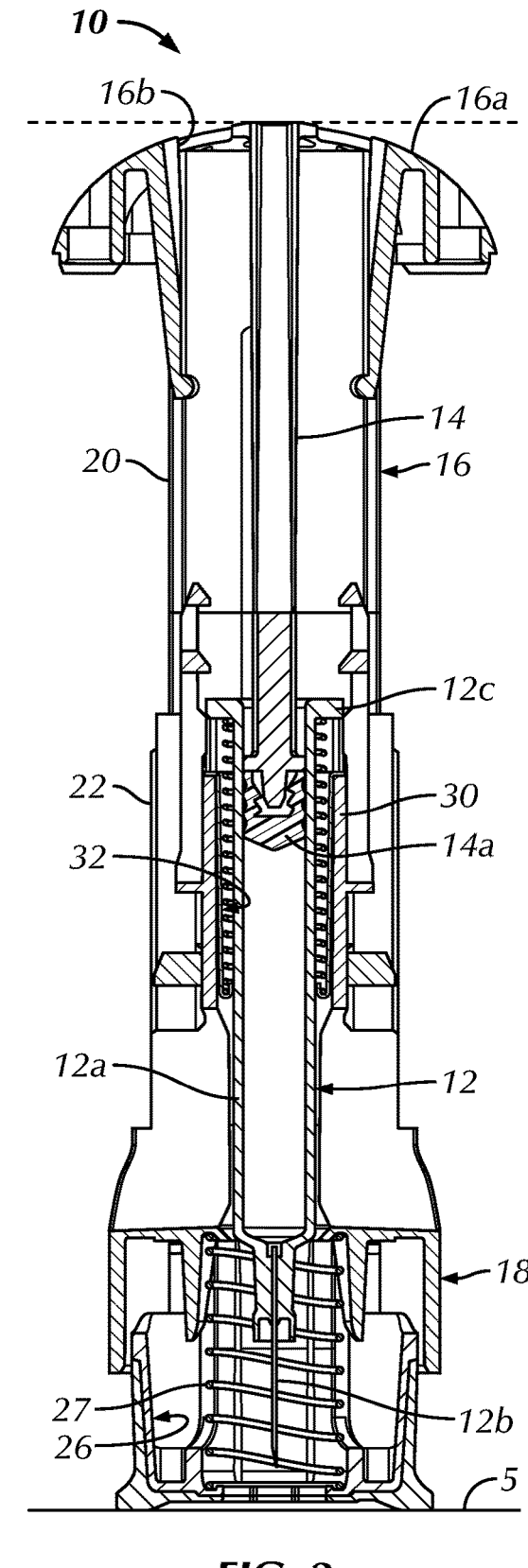
FIG. 1 is a cross-sectional elevational view of an injection device in a pre-use configuration according to the present disclosure.
FIG. 2 is a cross-sectional elevational view of the injection device of FIG. 1 placed on a skin surface, with a needle shield removed.

Certain terminology is used in the following description for convenience only and is not limiting. The words "lower," "bottom," "upper" and "top" designate directions in the drawings to which reference is made. The words "inwardly," "outwardly," "upwardly" and "downwardly" refer to directions toward and away from, respectively, the geometric center of the injector, and designated parts thereof, in accordance with the present disclosure. In describing the injection device, the term proximal is used in relation to the upper end of the device and the term distal is used in relation to the bottom surface of the device. Unless specifically set forth herein, the terms "a," "an" and "the" are not limited to one element, but instead should be read as meaning "at least one." The terminology includes the words noted above, derivatives thereof and words of similar import.

It should also be understood that the terms "about," "approximately," "generally," "substantially" and like terms, used herein when referring to a dimension or characteristic of a component of the disclosure, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to the drawings in detail, wherein like numerals indicate like elements throughout, there is shown in FIGS. 1-7 an injection device 10, such as, for example, a palm-actuated, manual injector containing a prefilled syringe 12 having a syringe barrel 12*a* with an injection needle 12*b* at a distal end thereof and a flange 12*c* radially extending from an open proximal end thereof. The injection device 10 includes an upper housing 16 and a lower housing 18, which, as will be described in further detail below, are configured to be movable, e.g., slidable, with respect to each other in a longitudinal direction during an injection. The prefilled syringe 12 may be at least partially retained coaxially within the lower housing 18 such that the injection needle 12*b* protrudes from a distal end of the lower housing 18. The upper housing 16 may include an upper shell (not shown) and the lower housing 18 may include a lower shell (not shown). The upper and lower shells may surround and prevent user access to particular internal components of the corresponding upper and lower housings 16, 18.

In the illustrated embodiment, the upper housing 16 includes a head portion 16*a* at a proximal end thereof. Optionally, the upper housing 16 may also be provided with a grip cap (not shown), which may be affixed to the head portion 16*a* to facilitate handling and actuation of the injection device 10 by a user. In the embodiment shown, the head portion 16*a* of the upper housing 16 can include a plunger rod 14 extending longitudinally therefrom and into the open proximal end of the barrel 12*a* of the prefilled syringe 12, such that distal movement of the upper housing 16 toward the distal end of the lower housing 18 moves the plunger rod 14 distally therewith to advance through the barrel 12*a* of the syringe 12 and expel medicament (not shown) from the syringe 12 via the injection needle 12*b*. Alternatively, the grip cap may include a plunger rod 14 which extends longitudinally and distally through the upper housing 16 and into an open proximal end of the prefilled syringe 12. Further alternatively, the prefilled syringe 12 may include a plunger rod 14 which is acted upon by a corresponding element (not shown) of the upper housing 16 and/or grip cap. The head portion 16*a* may include a proximal opening 16*b* that is sized and shaped to allow the plunger rod 14 to be inserted therethrough. The opening 16*b* may also be sized and shaped to allow insertion of the prefilled syringe 12 into the lower housing 18 during assembly of the injection device 10.

The syringe 12 may be provided with a piston 14*a* positioned within the syringe barrel 12*a* that is contacted/engaged by the plunger rod 14 during distal advancement of the plunger rod 14, or the piston 14*a* may take the form of a plunger head of the plunger rod 14. The piston 14*a* seals the medicament within the syringe barrel 12*a* on a proximal side of the medicament.

The injection device 10 further includes a needle guard 26 at least partially coaxially oriented, and in longitudinally slidable engagement with, the lower housing 18. The needle guard 26 is biased, e.g., by a coil needle guard spring 27 or the like (e.g., a different spring design, a compressed gas actuator, a hydraulic drive, a wax actuator, an electrochemical actuator, a shape memory alloy, and combinations thereof) such that a distal end of the needle guard 26 extends distally beyond the distal end of the lower housing 18 and beyond the distal tip of the injection needle 12*b* in one or more extended positions to prevent access to the tip of the injection needle 12*b*. However, to allow for an injection, the needle guard 26 may be moved proximally toward the distal end of the lower housing 18 into a retracted/second position thereof, such as when the distal end of the needle guard 26 is pressed against the skin surface of a user/patient, thereby exposing the distal tip of the injection needle 12*b*. A needle shield 28 (see FIG. 1), e.g., a rigid needle shield, may be removably attached to the syringe 12 and/or to the injection needle 12*b* to initially cover the injection needle 12*b*. In one configuration, a needle shield puller (not shown) may be coupled to the needle shield 28, whereby removal of the needle shield puller, e.g., from the lower housing 18 or the needle guard 26, causes the needle shield 28 to detach from the prefilled syringe 12 and expose the injection needle 12*b* for use.

In use, the injector device 10 is actuatable through various stages leading up to injection of the medicament, and automatic shielding of the injection needle 12*b* after injection is completed. FIG. 1 shows the injection device 10 in a pre-use configuration, e.g., as the device may be received by a user. In the pre-use configuration of the injection device 10, the upper housing 16 is oriented in a pre-use/original position and the needle guard 26 is in the extended/first position. In the extended position, the distal end of the needle guard 26 extends beyond the distal end of the lower housing 18 and is spaced from a proximal end of the lower housing 18 by a first interval. Positioning of the needle guard 26 in the extended position may prevent the upper housing 16 from distal movement relative to the lower housing 18 toward a dispensed position of the upper housing 16 in a manner such as described, for example, in U.S. Pat. No. 9,233,213, entitled "Palm Activated Drug Delivery Device" ("the '213 patent"), and International Application Publication No. WO 2021/030066, entitled "Palm Activated Drug Delivery Device" ("the '066 publication"), the entire contents of each of which are incorporated by reference herein.

A preliminary step in using the injection device 10 is to remove the needle shield 28, e.g., via a needle shield puller (not shown). As shown in FIG. 2, a distal end of the injection device 10 may then be placed by a user against the skin surface 5 of the user/patient at the desired injection location. As the upper housing 16 initially remains locked in the pre-use position, downward/distal force applied by the user onto the upper housing 16 moves the needle guard 26 proximally with respect to the lower housing 18, i.e., upwardly, from the extended position thereof (FIGS. 1, 2) to the retracted position thereof (FIG. 3). In the retracted position, the needle guard 26 is spaced from the proximal end of the lower housing 18 by a second interval that is less than the first interval and exposes and allows the injection needle 12*b* to penetrate the user's skin to a first depth, e.g., subcutaneously. Movement of the needle guard 26 into the retracted position thereof also unlocks the upper housing 16, in a manner such as described, for example, in the '213 patent or the '066 publication and enables subsequent distal movement of the upper housing 16 relative to the lower housing 18.

Subsequently, maintained application of downward/distal force onto the upper housing 16 by the user moves the upper housing 16 distally relative to the lower housing 18 from the pre-use position (FIGS. 1-3) to a ready-to-dispense position (FIG. 4). Distal movement of the upper housing 16 from the pre-use position to the ready-to-dispense position also translates the syringe 12 distally therewith relative to the lower housing 18 (as will be described in further detail below), thereby further advancing the injection needle 12*b* into the user's skin to a second depth, e.g., an intramuscular depth (FIG. 4).

As shown in FIG. 5, further continued application of downward/distal force onto the upper housing 16 by the user further moves the upper housing 16 distally relative to the lower housing 18 from the ready-to-dispense position toward the dispensed position thereof. As shown between FIGS. 4 and 5, distal movement of the upper housing 16 relative to the lower housing 18 from the ready-to-dispense position toward the dispensed position thereof advances the plunger rod 14 and the piston 14*a* through the syringe barrel

12*a*, thereby dispensing the medicament within the syringe barrel 12*a* through the injection needle 12*b* to the user/patient.

As shown in FIG. 6, the user ceases application of downward/distal force onto the upper housing 16 when the upper housing 16 reaches the end of its travel, i.e., the dispensed position thereof, and medicament injection is complete. The needle guard spring 27 may, in turn, re-expand, withdrawing the injection needle 12*b* from the skin of the user/patient, and returning the needle guard 26 at least to the extended position thereof (or beyond to a third, further distal position, in a manner such as described, for example, in the '213 patent or the '066 publication) to extend over the injection needle 12*b*, protecting the user and others from accidental needle punctures. The user may also actively remove the injection device 10 from the skin surface 5, thereby also permitting the needle guard 26 to extend over the injection needle 12*b* under the force of the needle guard spring 27. Once the needle guard 26 is fully extended, a needle guard lock (not shown) may prevent the needle guard 26 from retracting again, in a manner such as described, for example, in the '213 patent or the '066 publication. Optionally, as shown in FIGS. 5 and 6, the upper housing 16 may also lock in place with the lower housing 18 in the dispensed position thereof, in a manner such as described, for example, in the '213 patent or the '066 publication, to prevent resetting or reuse of the injection device 10.

Figure 7:
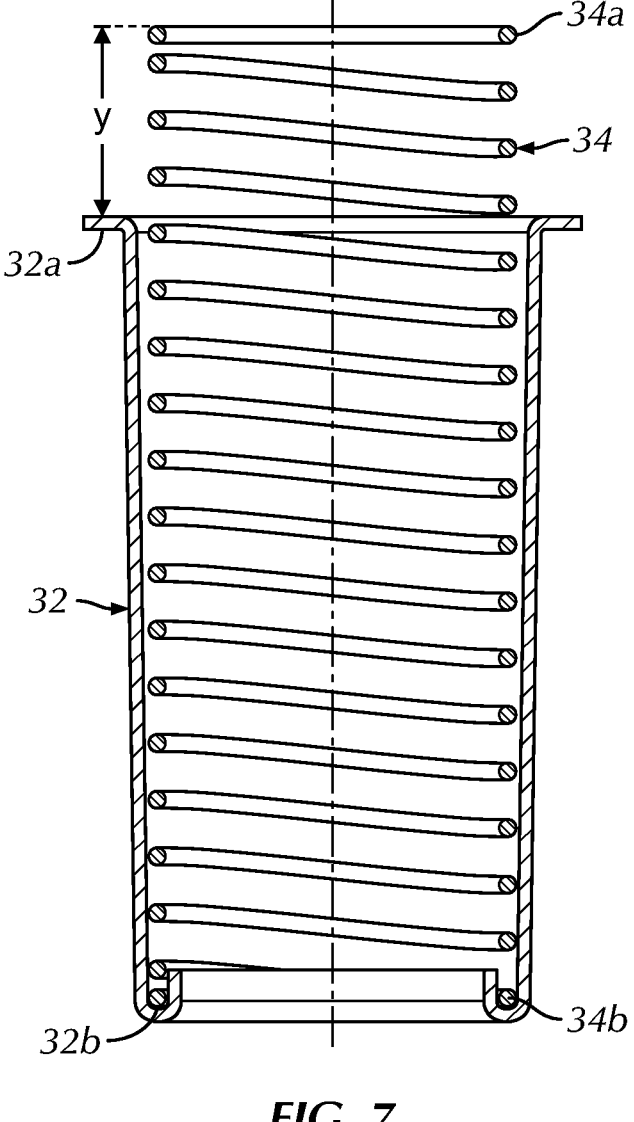
FIG. 7 is an enlarged, cross-sectional elevational view of a sleeve and syringe spring of the injection device of FIG. 1, with the syringe spring in a relaxed, substantially uncompressed state.

Referring to FIGS. 3, 4 and 7, distal movement of the upper housing 16 from the pre-use position to the ready-to-dispense position, which translates the syringe 12 distally therewith relative to the lower housing 18, will now be described in detail. As shown best in FIGS. 3 and 4, the syringe 12 is supported by an open-ended channel 30 formed within the lower housing 18. An open-ended sleeve 32 may be at least partially coaxially received within the channel 30. The sleeve 32 is mounted in a stationary manner within, and relative to, the lower housing 18. In the illustrated embodiment, as shown best in FIG. 7, the sleeve 32 has a radially outwardly flanged proximal rim 32*a*, which may be supported by a ledge surrounding a proximal end of the channel 30, or alternatively by another portion of the lower housing 18. An outer diameter of the sleeve 32 is configured to mate in a substantially fitted engagement with an inner diameter of the channel 30, such that the sleeve 32 may be mounted in the channel 30 in a stable manner.

The sleeve 32 also includes a radially inwardly extending annular lip 32*b* at a distal end thereof. In the illustrated embodiment, the annular lip 32*b* is rolled in, creating an annular pocket, but the disclosure is not so limited. The annular lip 32*b* generally serves as a support for a syringe spring 34 mounted within the sleeve 32, wherein a distal end 34*b* of the syringe spring 34 is received by the distal annular lip 32*b* (e.g., within the distal pocket) of the sleeve 32. A proximal end 34*a* of the syringe spring 34 generally extends a distance Y proximally beyond the proximal end 32*a* of the sleeve 32 in a relaxed, substantially uncompressed state of the syringe spring 34. When installed, the syringe barrel 12*a* extends through the syringe spring 34 and the sleeve 32 and an underside of the flange 12*c* of the syringe 12 may be supported by the proximal end 34*a* of the syringe spring 34. The inner diameter of the sleeve 32 and corresponding diameter of the syringe spring 34 are configured to receive the syringe barrel 12*a* in a stable, concentric manner.

In operation, and as shown in FIGS. 1-3, the syringe 12 is initially mounted within the lower housing 18 in a first position, wherein the syringe 12 is supported by the syringe spring 34 in the relaxed, substantially uncompressed state of the syringe spring 34. The length of the syringe spring 34 in the relaxed, substantially uncompressed state thereof, in combination with the length of the syringe 12 (including the length of the injection needle 12b), is configured/selected to appropriately position the syringe 12 (and the injection needle 12b thereof), to approximately penetrate the skin surface 5 of a user/patient to a predetermined first depth, e.g., a subcutaneous depth, when the needle guard 26 is moved from the extended position to the retracted position thereof. In one non-limiting configuration, the first depth may be approximately less than 10 mm.

The stiffness of the syringe spring 34 is configured such that the force required to compress the syringe spring 34 is less than the force of static friction between the piston 14a and the syringe barrel 12a which must be overcome for the piston 14a to advance distally within the syringe barrel 12a. Accordingly, distal movement of the upper housing 16 from the pre-use position to the ready-to-dispense position (as shown in FIGS. 3, 4), which moves the plunger rod 14 therewith, compresses the syringe spring 34 prior to effecting advancement of the plunger rod 14 and the piston 14a through the syringe barrel 12a. As shown, the syringe spring 34 compresses until the proximal flange 12c of the syringe 12 engages the proximal end 32a of the sleeve 32, which corresponds to distally translating the syringe 12 relative to the lower housing 18 by approximately the distance Y. Distal translation of the syringe 12 relative to, and through, the lower housing 18 by approximately the distance Y positions the syringe 12 in a distal-most position thereof and advances the injection needle 12b further beneath the skin surface 5 of the user/patient to a predetermined second depth, e.g., an intramuscular depth, such as, for example, between approximately another 10 mm and approximately another 80 mm deeper, depending on factors, such as, for example, user/patient age, injection site location, fat distribution, a combination thereof and the like. In one non-limiting configuration, the second depth may be between approximately 10 mm and approximately 12 mm.

As should be understood, the syringe spring 34 may alternatively compress until the force required to compress the syringe spring 34 exceeds the force of static friction between the piston 14a and the syringe barrel 12a, which may also be configured to correspond to distally translating the syringe 12 sufficiently to penetrate the injection needle 12b under the skin surface 5 of the user/patient to the predetermined second depth. That is, the stiffness of the syringe spring 34 and/or the force of static friction between the piston 14a and the syringe barrel 12a may be configured to distally translate the syringe 12 the required amount to obtain the predetermined second depth, e.g., without the need to physically obstruct further distal movement of the syringe 12. Subsequent additional distal movement of the upper housing 16 from the ready-to-dispense position toward the dispensed position (as shown in FIG. 5), advances the plunger rod 14 and the piston 14a through the stationary syringe barrel 12a, to, in turn, dispense the medicament within the syringe barrel 12a through the injection needle 12b to the user/patient.

Advantageously, configuring the syringe 12 to be distally movable within the lower housing 18 in addition to movement of the needle guard 26 in order to inject the injection needle 12b to the predetermined, selected depth beneath the skin surface 5 provides greater flexibility in achieving the objective injection needle 12b depth. For example, the same injection device 10 may accommodate different sized, e.g., different length, syringes 12 and/or injection needles 12b while maximizing the number of common injection device 10 components. That is, the upper housing 16, the lower housing 18 and the needle guard 26 may remain the same while the appropriate length of the sleeve 32 and of the syringe spring 34 may be selected to accommodate different length syringes 12 and/or injection needles 12b, in order to achieve the objective depth beneath the skin surface 5. For example, a shorter syringe 12 may require a greater distance Y, i.e., in order to permit greater distal movement by the syringe 12 to achieve the objective injection needle 12b depth under the skin surface 5. A greater distance Y may be achieved, for example, without limitation, via a shorter sleeve 32, a longer syringe spring 34, or a combination thereof. The length of the sleeve 32 and/or the syringe spring 34 may alternatively be configured to initially position the needle 12 relative to the lower housing 18 and the needle guard 26 such that movement of the needle guard 26 from the extended position to the retracted position thereof only brings the injection needle 12b closer to the skin surface 5 of the user/patient (without penetration), and subsequent compression of the syringe spring 34 distally advances the syringe 12 relative to the lower housing 18 and the needle guard 26 to penetrate the skin surface 5 with the injection needle 12b to an objective depth, e.g., subcutaneous, intramuscular, or beyond.

Optionally, the stiffness of the syringe spring 34 controlling distal movement of the syringe 12 may be greater than the stiffness of the needle guard spring 27 within the needle guard 26, thereby requiring the needle guard 26 to move first to unlock the upper housing 16. Alternatively, the upper housing 16 may not be locked in place relative to the lower housing 18 in the pre-use configuration of the injection device 10, but rather, the stiffness of the syringe spring 34 controlling distal movement of the syringe 12 being greater than the stiffness of the needle guard spring 27 within the needle guard 26 requires the needle guard 26 to move from the extended position to the retracted position, i.e., compressing the needle guard spring 27, prior to compression of the syringe spring 34, i.e., distal movement of the upper housing 16.

It will be appreciated by those skilled in the art that various modifications and alterations could be made to disclosure above without departing from the broad inventive concepts thereof. Some of these have been discussed above and others will be apparent to those skilled in the art. It is understood, therefore, that this invention is not limited to the particular embodiments disclosed, but it is intended to cover modifications within the spirit and scope of the present disclosure, as set forth in the appended claims.

I claim:

1. An injection device configured to administer a medicament from a syringe having a syringe barrel at least partially filled with the medicament and sealed by a piston, a flange extending radially from a proximal end of the syringe barrel, and a needle extending distally from a distal end of the syringe barrel, the injection device comprising:

a lower housing;

a spring retaining sleeve supported by the lower housing;

a syringe spring at least partially received within the spring retaining sleeve, wherein the syringe spring is configured to support an underside of the flange of the syringe when installed to support the syringe within the lower housing such that the needle protrudes from a distal end of the lower housing;

a needle guard in sliding engagement with the lower housing, the needle guard being movable relative to the lower housing in a proximal direction from:

a first position in which a distal end of the needle guard extends beyond the distal end of the lower housing, the distal end of the needle guard is spaced from a proximal end of the lower housing by a first interval, and the distal end of the needle guard is configured to conceal a distal tip of the needle when the syringe is installed in the lower housing, to a second position in which the distal end of the needle guard is spaced from the proximal end of the lower housing by a second interval that is less than the first interval;

a needle guard spring configured to engage the lower housing and the needle guard to bias the needle guard distally relative to the lower housing; and an upper housing in sliding engagement with the lower housing and movable relative to the lower housing in a distal direction from a pre-use position to a dispensed position, wherein:

proximal movement of the needle guard from the first position to the second position is configured to extend the distal tip of the needle distally beyond the needle guard by a first distance when installed, and subsequent distal movement of the upper housing relative to the lower housing from the pre-use position toward the dispensed position is configured to (i) first compress the syringe spring, and, in turn, distally translate the needle relative to the lower housing when installed, such that the distal tip of the needle extends distally beyond the needle guard by a second distance that is greater than the first distance, and (ii) thereafter, further advance the upper housing distally relative to the syringe when installed to dispense the medicament from the syringe.

2. The injection device of claim 1, wherein the spring retaining sleeve defines:

a passage, the syringe spring being positioned at least partially within the passage, and a support disposed within the passage to support a distal end of the syringe spring.

3. The injection device of claim 1, wherein the syringe spring has a stiffness resulting in a spring compression force that is less than a force of static friction between the piston and the syringe barrel when the syringe is installed within the lower housing.

4. The injection device of claim 1, wherein the distal movement of the upper housing relative to the lower housing is configured to translate therewith a plunger rod engaging the piston, wherein distal translation of the plunger rod first causes the compression of the syringe spring, and subsequently advances the piston through the syringe barrel to dispense the medicament from the syringe.

5. The injection device of claim 1, wherein the upper housing is positionally locked relative to the lower housing when the upper housing is in the dispensed position.

6. The injection device of claim 5, wherein the needle guard spring is configured to bias the needle guard from the second position to a third position when the upper housing is locked in the dispensed position, wherein, in the third position:

the distal end of the needle guard extends beyond the distal end of the lower housing, the distal end of the needle guard is spaced from the proximal end of the lower housing by a third interval greater than the first interval, and the distal end of the needle guard is configured to conceal the distal tip of the needle of the syringe when installed.

7. The injection device of claim 6, wherein the needle guard is positionally locked relative to the upper housing and the lower housing in the third position thereof.

8. The injection device of claim 1, wherein the first distance is less than 10 mm.

9. The injection device of claim 1, wherein the second distance is at least 10 mm greater than the first distance.

10. The injection device of claim 9, wherein the second distance is between approximately 10 mm and approximately 80 mm.

11. The injection device of claim 1, further comprising the syringe installed within the lower housing.

12. The injection device of claim 1, wherein the upper housing is prevented from distal movement relative to the lower housing when the needle guard is in the first position.

13. The injection device of claim 12, wherein proximal movement of the needle guard from the first position to the second position is enables distal movement of the upper housing relative to the lower housing.

* * * * *